(12) United States Patent
Bathe

(10) Patent No.: US 7,152,597 B2
(45) Date of Patent: Dec. 26, 2006

(54) BREATHING CIRCUIT ADAPTER

(75) Inventor: Duncan P. L. Bathe, Fitchburg, WI (US)

(73) Assignee: Datex-Ohmeda, Inc., Madison, WI (US)

( * ) Notice: Subject to any disclaimer, the term of this patent is extended or adjusted under 35 U.S.C. 154(b) by 618 days.

(21) Appl. No.: 10/671,094

(22) Filed: Sep. 25, 2003

(65) Prior Publication Data

US 2005/0066964 A1 Mar. 31, 2005

(51) Int. Cl.
*A62B 9/04* (2006.01)

(52) U.S. Cl. .................. 128/202.27; 128/911; 128/912

(58) Field of Classification Search ........... 128/200.14, 128/200.21, 201.13, 203.12, 203.16, 203.17, 128/203.18, 204.18, 204.23, 205.24, 202.27, 128/911, 912
See application file for complete search history.

(56) References Cited

U.S. PATENT DOCUMENTS

| | | | |
|---|---|---|---|
| 3,865,106 A | 2/1975 | Palush | |
| 4,521,038 A * | 6/1985 | Cerny | 285/24 |
| 4,676,239 A * | 6/1987 | Humphrey | 128/205.17 |
| 4,712,580 A | 12/1987 | Gilman et al. | |
| 4,941,469 A | 7/1990 | Adahan | |
| 5,020,532 A | 6/1991 | Mahoney et al. | |
| 5,121,746 A * | 6/1992 | Sikora | 128/203.12 |
| 5,127,400 A | 7/1992 | DeVries et al. | |
| 5,617,847 A * | 4/1997 | Howe | 128/204.23 |
| 5,771,884 A | 6/1998 | Yarnall et al. | |
| 5,823,184 A * | 10/1998 | Gross | 128/204.18 |
| 5,983,896 A * | 11/1999 | Fukunaga et al. | 128/207.14 |
| 6,073,630 A | 6/2000 | Adahan | |
| 6,098,622 A | 8/2000 | Nobile et al. | |
| 6,102,038 A | 8/2000 | DeVries | |
| 6,123,674 A | 9/2000 | Rich | |
| 6,516,800 B1 | 2/2003 | Bowden | |
| 6,874,500 B1 * | 4/2005 | Fukunaga et al. | 128/204.18 |
| 2002/0148468 A1 | 10/2002 | Vatelj | |

FOREIGN PATENT DOCUMENTS

EP 1 238 681 9/2002

* cited by examiner

*Primary Examiner*—Henry Bennett
*Assistant Examiner*—Amadeus Lopez
(74) *Attorney, Agent, or Firm*—Andrus, Sceales, Starke & Sawall, LLP

(57) ABSTRACT

An adapter couples a patient's breathing circuit to a ventilator. In the preferred embodiment, the adapter comprises an inhalation conduit having a first end for coupling the adapter to the ventilator and a second end for coupling the adapter to the patient breathing circuit; an exhalation conduit having a first end for coupling the adapter to the patient breathing circuit and a discharge conduit, the discharge conduit transversely oriented to the inhalation conduit; an exhaust port communicating with the discharge conduit for releasing breathed gas from same; a valve selectively opening and closing the discharge conduit to release gas from same; and a base comprising means for releasably coupling the adapter to the ventilator.

17 Claims, 5 Drawing Sheets

BREATHING CIRCUIT ADAPTER

BACKGROUND OF THE INVENTION

The present invention is directed to an adapter for coupling a patient breathing circuit to a ventilator. In the preferred embodiment, the present invention relates to a breathing circuit adapter for interconnecting a patient's breathing circuit, a pressure monitor, a source of aerosolized medicine and a ventilator.

Patients that have ventilatory difficulties are often placed on a ventilator. A ventilator is a mechanical device designed to provide all or part of the work a body must produce to move gas into and out of the lungs. The ventilator delivers breathable gas to a patient and carries breathed gas from the patient through a set of flexible tubes called a patient breathing circuit. Typically, the patient breathing circuit connects the ventilator to an endotracheal or tracheostomy tube that extends into the patient's throat or to a mask covering the patient's mouth and/or nose. Such a connection is often made via a Y-piece connector, which unites the inhalation and exhalation conduits and provides a means for permitting gas flow in either conduit based upon whether patient inhalation or exhalation is occurring. The endotracheal tube or tracheotomy tube may include a balloon cuff to provide a seal inside the trachea for the tracheal tubes or a mask may have a seal around the mouth and nose to sustain a predetermined air pressure within the circuit and patient lungs.

Most ventilators have at least one pressure monitor that measures patient airway pressures to gauge the pressure of the breathing gas delivery and whether or not the patient is properly connected to the ventilator. Many ventilators have sophisticated pressure, volume and flow sensors that produce signals both to control the ventilator output and to provide displays of how the ventilator and patient are interacting.

To medicate a patient on a ventilator, aerosolized medicine is often installed into the breathing circuit. A device for delivering aerosolized medicine, such as a nebulizer, introduces the aerosoled medication periodically as prescribed into the breathable gas flowing through the inspiratory conduit of the patient circuit and ultimately to the patient's airway and lungs. As with any dispensation of medication to a patient, it is desirable to provide a delivery device/ventilator/breathing circuit adapter that optimizes dosage control and maximizes deposition of aerosolized medicine in the inhaled gas.

Typically, devices for delivering aerosolized medicine, such as nebulizers, have been coupled to the patient circuit proximate to the patient interface (i.e. the endotracheal or tracheostomy tube or mask) at the Y-piece connector. However, recent studies have concluded that in many instances coupling the nebulizing device to the patient circuit proximate to the ventilator provides better deposition of aerosolized medicine during the inhalation phase. During the exhalation phase the ventilator, or nebulizer, provides a small bias flow rate while the nebulizing device continuously atomizes medicine at a fixed rate. With the nebulizer placed proximate to the ventilator (at the distal end of the inspiratory circuit relative to the patient), the bias flow charges the inspiratory circuit with aerosol during the expiratory phase. In contrast, aerosol generated with the nebulizer positioned at the patient Y-piece is directed down the expiratory conduit of the patient circuit during the exhalation phase, reducing the amount of medicine available to the patient.

For the foregoing reasons, an efficient means for coupling a patient breathing circuit to a ventilator is desirable. An efficient means for coupling a delivery device for aerosolized medicine to a patient breathing circuit proximate to a ventilator is also greatly desired. Specifically, it is desirable to provide a breathing circuit adapter for interconnecting a delivery device for aersolized medicine, such as a nebulizer, proximate to a ventilator and distal from the patient relative to the inspiratory circuit, thus maximizing efficiency and the amount of medicine provided to the patient. It is desirable to provide such a breathing circuit adapter which is simple, easy to use, and comprises minimal parts to therefore minimize chances for mechanical breakdown.

SUMMARY OF THE INVENTION

The present invention provides an efficient means for coupling a patient breathing circuit to a ventilator. The present invention also provides an efficient means for coupling a delivery device for aerosolized medicine, such as a nebulizer, to a patient breathing circuit proximate to the ventilator.

The adapter includes an inhalation conduit having a first end for coupling the adapter to the ventilator and a second end for coupling the adapter to the patient breathing circuit; an exhalation conduit having a first end for coupling the adapter to the patient breathing circuit and a discharge conduit, the discharge conduit transversely oriented to the inhalation conduit; an exhaust port communicating with the discharge conduit for releasing breathed gas from same; a valve selectively opening and closing the discharge conduit to release gas from same; and a base comprising means for releasably coupling the adapter to the ventilator.

In the preferred embodiment, the adapter also includes a pressure sensing port for interconnecting a ventilator monitor with a monitoring port that is located in the breathing circuit proximate to the patient. A medicine delivery conduit communicates with the inhalation conduit intermediate its first and second ends and receives medicine and provides same to the inhalation conduit.

The adapter is releasably mounted to the ventilator. Means for releasably mounting the adapter to the ventilator may include a camming mechanism that is manually actuated by the caregiver to uncouple the adapter from the ventilator.

The adapter efficiently unites the necessary components for treating a patient on a ventilator with medicine. In one embodiment, the adapter is uniquely designed to couple the source of aerosolized medicine proximate to the ventilator and in a vertical orientation to provide better deposition of liquid aerosolized medicine during the inhalation phase of the patient's breathing cycle.

BRIEF DESCRIPTION OF THE DRAWINGS

FIG. 1 is a perspective view of the adapter of the present invention.

FIG. 2 is a side view of the adapter.

FIG. 3 is a sectional view of the adapter taken along section 3—3 shown in FIG. 1.

FIG. 4 is a sectional view of the adapter taken along section 4—4 shown in FIG. 3.

FIG. 5 is a sectional view of the adapter taken along section 5—5 shown in FIG. 1.

DETAILED DESCRIPTION OF THE PREFERRED EMBODIMENT

In the preferred embodiment of the present invention described in detail below, an adapter for a ventilation system employing a source of aerosolized medicine interconnects a patient's breathing circuit, a pressure monitor, a source of aerosolized medicine and a ventilator. It should be understood that the drawings and specification are to be considered an exemplification of the principles of the invention, which is more particularly defined in the appended claims. For example, although an adapter having coaxial breathing conduits is shown, it is contemplated that an adapter having non-coaxial or separate conduits is contemplated. In addition, although the adapter shown employs a source of aerosolized medicine, it is understood that an adapter without means for coupling to a source of aerosolized medicine is conceived.

Figure 1:
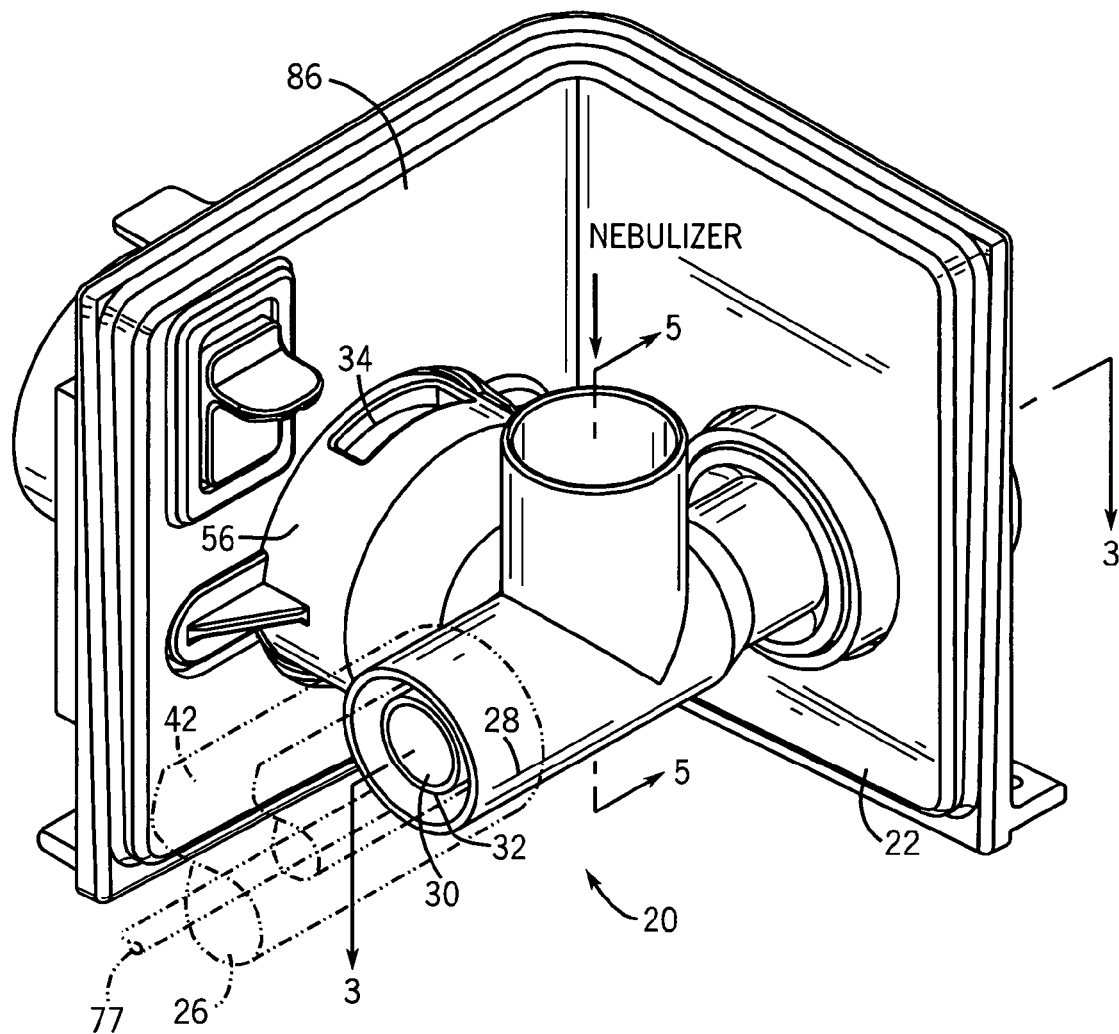

As shown in FIG. 1, the adapter 20 of the present invention is mounted to a ventilator 22. The adapter 20 is designed to facilitate coupling of a source of aerosolized medicine, namely a nebulizer 24 (illustratively shown in FIGS. 2 and 5) to a patient breathing circuit 26 proximate to the ventilator 22. As described above, placement of the nebulizer 24 proximate to the ventilator 22 provides improved deposition of aerosolized medicine during a patient inhalation phase. Although in the preferred embodiment shown, the nebulizer 24 provides a source of aerosolized medicine to the breathed gas, it is contemplated that the adapter may be designed to function either with or without a variety of known delivery devices for aerosolized medicine.

The adapter 20 is further designed to couple the nebulizer 24 in a vertical orientation, as shown. The vertical orientation is preferred for the nebulizer 24 to efficiently facilitate dispensation of liquid aerosolized medication to the patient, as is well known in the art.

Figure 2:
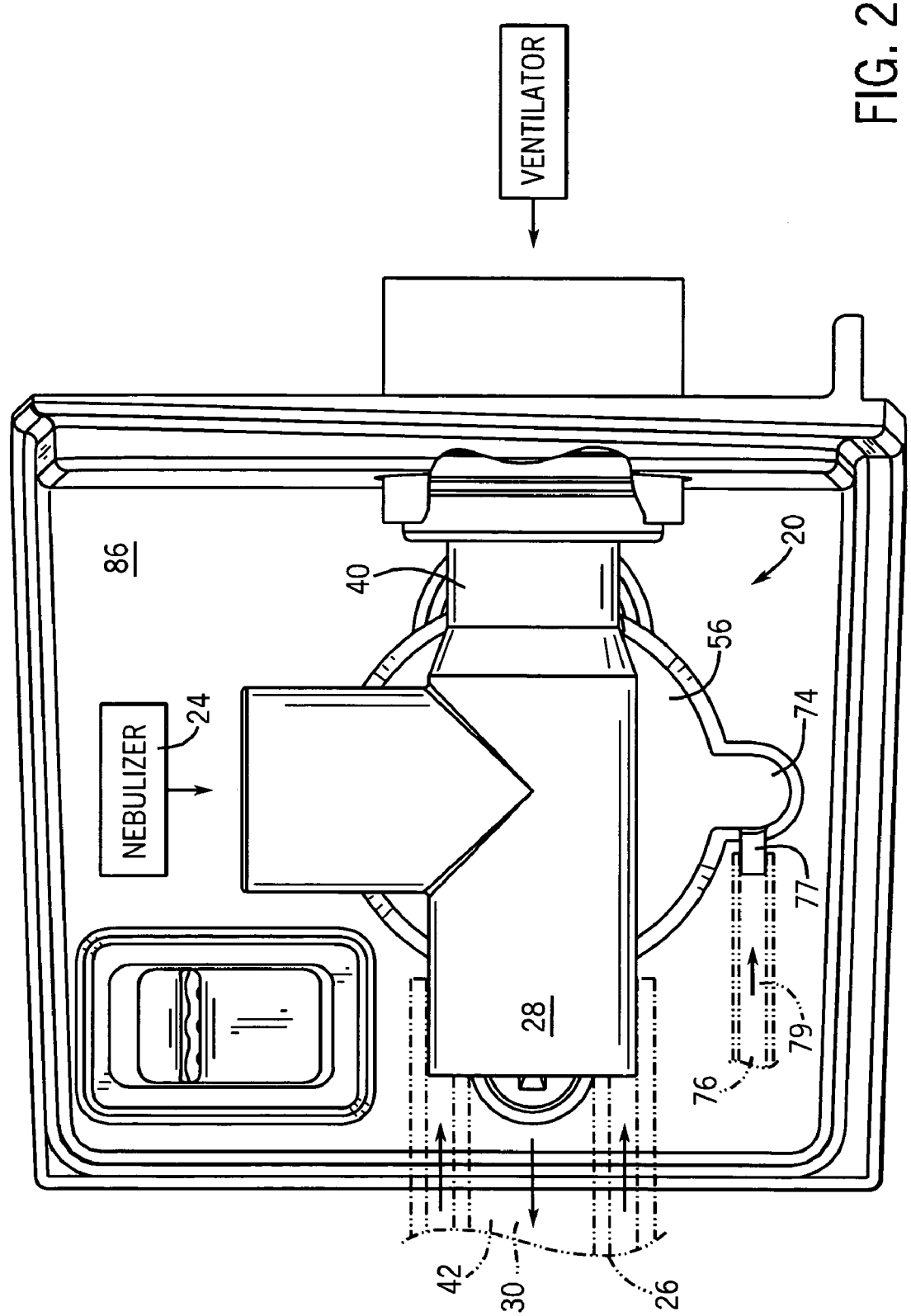
Figure 3:
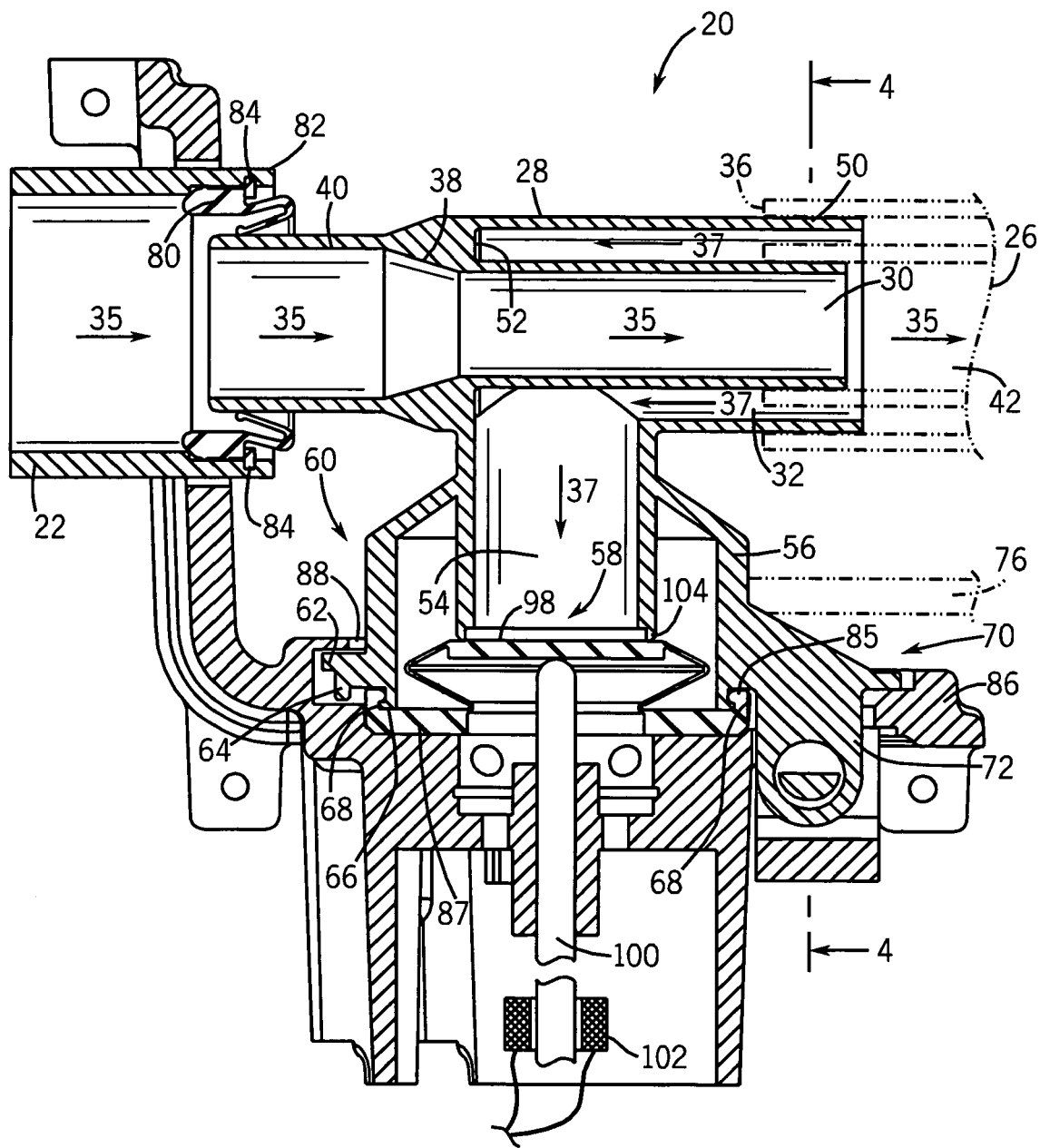

As shown in FIGS. 1–3, the adapter 20 of the present invention includes several components. The adapter 20 includes coaxial breathing conduits 28 including a central inhalation conduit 30 and surrounding exhalation conduit 32. The coaxial breathing conduits 28 in the particular embodiment shown are tubular and designed to facilitate gas flow from the ventilator 22 to the patient breathing circuit 26, and then back from the patient breathing circuit 26 to an exhaust port 34, as shown in FIG. 3 by arrows 35 and 37. It should be recognized that the coaxial breathing conduits 28 may comprise a variety of shapes and sizes and are not limited by the particular shape depicted in the drawings.

Referring to FIG. 3, the central inhalation conduit 30 has a first end portion 36 for coupling the adapter 20 to the patient breathing circuit 26, an outwardly tapered portion 38, and a second end portion 40 for coupling the adapter to the ventilator 22. As will be explained further below, when the adapter 20 interconnects the ventilator 22 and the patient breathing circuit 24, breathable gas flows from the ventilator 22, through the central inhalation conduit 30, to the inhalation tube 42 of the patient breathing circuit 26, as shown by arrows 35.

Figure 5:
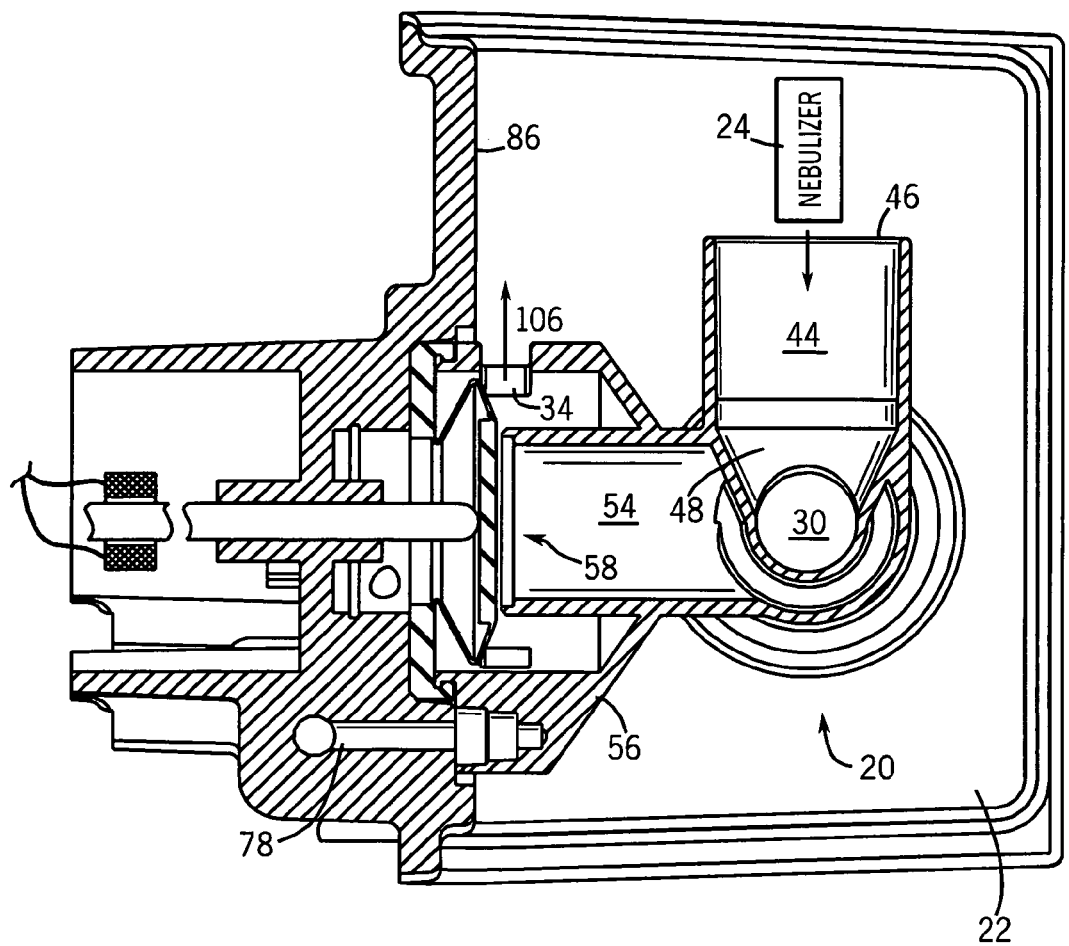

Referring briefly to FIG. 5, the adapter 20 further includes a medicine delivery or nebulizer conduit 44 designed to facilitate flow of aerosolized medicine from the nebulizer 24 to the central inhalation conduit 30. The nebulizer conduit 44 extends orthogonally from the coaxial breathing conduits 28 and has a first end 46 for coupling to the nebulizer 24 and a second tapered end 48 connecting to the central inhalation conduit 30. As will be described further below, when breathable gas is flowing through the central inhalation conduit 30, the nebulizer 24 deposits aerosolized medicine to the nebulizer conduit 44 and into the breathable gas stream. The vertical orientation of the nebulizer 24 advantageously enhances the efficiency of dispensation of aerosolized medication to the patient breathing circuit 24, and thus to the patient.

Referring back to FIG. 3, the surrounding exhalation conduit 32 may extend along the same axis as the central inhalation conduit 30 and has a first end 50 for coupling the adapter 20 to the patient breathing circuit 26 and a second end 52 connecting to a depending discharge conduit 54. The depending discharge conduit 54 is shown as a tube that extends orthogonally from the exhalation conduit 32 and connects to a base 56 of the adapter 20.

The base 56 is an outwardly tapered member, which mounts the adapter 20 to the ventilator 22. The base 56 includes the exhaust port 34, shown in FIG. 5, for discharging breathed gas from the discharge conduit 54. Discharge conduit 54 is selectively opened and closed by a valve 58 which is preferably part of the adapter 20 and actuated by the ventilator 22. The structure and function of valve 58 will be described more fully below.

The exterior of the base 56 of the adapter 20 includes several features designed to facilitate simple removable mounting of the adapter 20 to the ventilator 22. As shown in FIG. 3, the rear portion 60 of the base 56 includes an outwardly extending peripheral lip 62 and a downwardly extending finger 64. The bottom rim 66 of the base 56 includes an outwardly extending lip 68. The front portion 70 of the base includes a downwardly extending keyhole 72. The function and structure of these elements will be further described below.

Referring briefly to FIG. 2, the adapter 20 further comprises a pressure sensing port 74 for interconnecting a monitoring port located proximal to the patient in the breathing circuit with a ventilator pressure sensor (not shown) via flexible tube 76. As is well known in the art, a pressure sensor output may be connected to a control system, which assures that the breathing pattern produced by the ventilator is the one intended by the patient's caregiver. The pressure sensing port 74 comprises a nipple 77, which is sized to fit snugly within the flexible tube 76 for the pressure monitoring port. Air pressure from the patient's airway is supplied to the tube 76 and passageway 78 (FIG. 5) and ultimately to the ventilator monitor in the direction shown by arrow 79.

Referring back to FIG. 3, a significant advantage of the adapter 20 of the present invention is that it may be quickly and easily connected to and disconnected from the ventilator 22. To connect the adapter 20 to the ventilator 22, the second end portion 40 of the central inhalation conduit 30 is inserted into and retained in a press-fit sealing relation by elastomeric sealing ring 80 on the ventilator outlet 82. Rim 84 on ventilator outlet 82 engages sealing ring 80, securing it to ventilator outlet 82.

As the second end portion 40 of the surrounding exhalation conduit 32 is inserted into the elastomeric ring 80, the base 56 of the adapter 20 is simultaneously mounted to surface 86 of ventilator 22. As shown in FIG. 3, the peripheral lip 62 of the base 56 is secured beneath a retaining ledge 88 on the surface 86 of the ventilator 22. Bottom rim 66 and peripheral lip 68 of the base 56 fits within retaining rim 85 of elastomeric seal 87. As such, a sealing relationship between the base 56 of the adapter 20 and the surface 86 of the ventilator 22 is formed. Finger 64 of the base 56 further prevents the adapter 20 from disconnecting from the ventilator 22.

Figure 4:
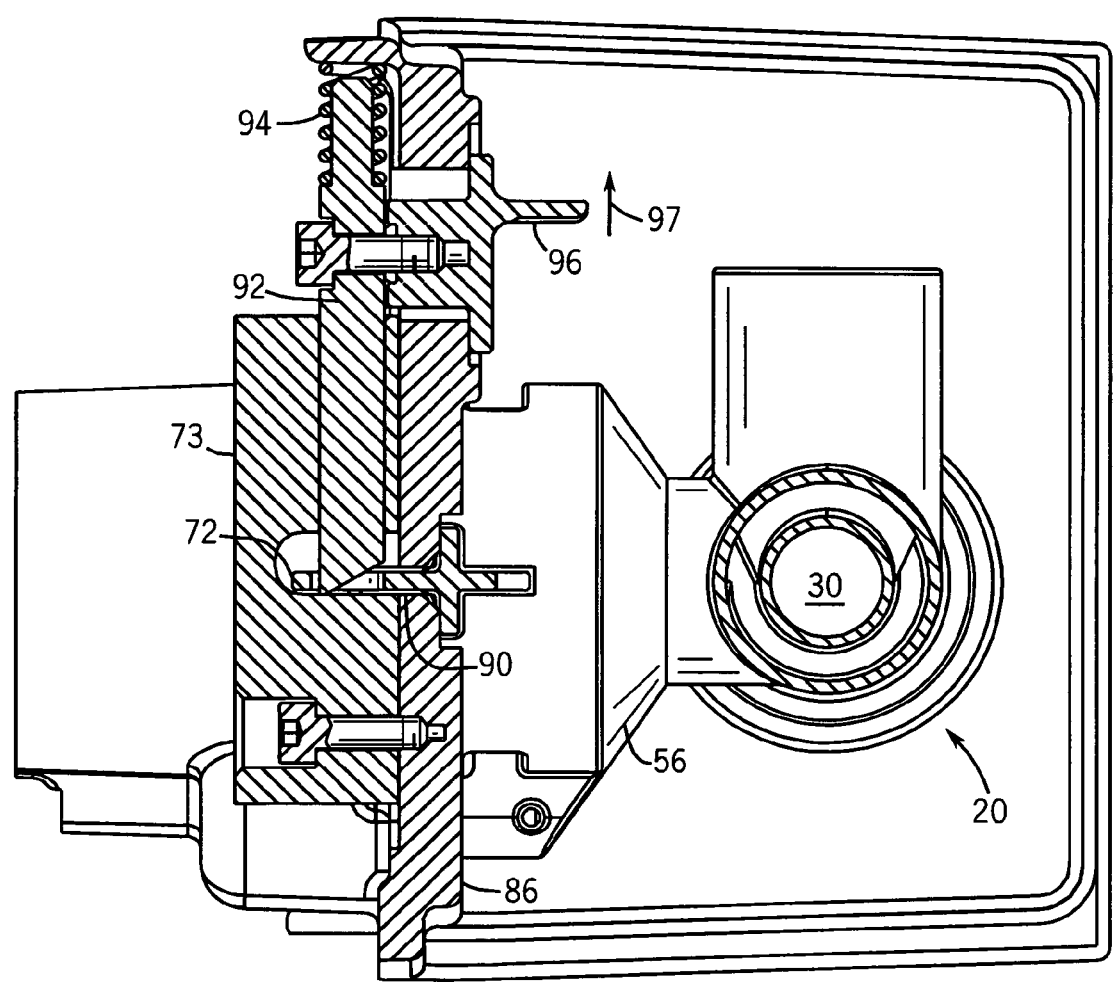

Referring to FIG. 4, as the peripheral lip 62 is inserted beneath the ledge 88, keyhole member 72 on the front portion 70 of the base is inserted into slot 90 in the surface 86 of the ventilator. Bar 92 is biased in a closed position by spring 94, and has an angled end surface 73. As keyhole member 72 is inserted into slot 90, bar 92 is cammed into an open position when keyhole member 72 engages angled end surface 73. As keyhole member 72 fully seats into slot 90, bar 92 is biased back into a closed position by spring 94, such that the angled end surface 73 passes through keyhole member 72. Once closed, the bar 92 and keyhole member 72 coupling secures the adapter base 56 to the ventilator 22.

Referring back to FIG. 2, once the adapter 20 is secured to the ventilator 22, the caregiver couples the patient breathing circuit 26 to the coaxial breathing conduits 28 and the flexible tube 76 to the pressure monitoring port 74 in a press-fit relationship. If a more permanent coupling is desired, the respective circuits may be bonded to the respective ports so that adapter 20 and breathing circuit 26 form an integral structure. Adapter 20 and breathing circuit 26 may be formed of a plastic material so as to be suitable for single use, disposable applications.

Referring back to FIG. 4, to remove the adapter 20 from the ventilator 22, the caregiver pulls the tab 96 in the direction of arrow 97 to move the bar 92 away from the adapter 20 and out of the keyhole member 72. The caregiver then removes the adapter 20 from the ventilator 22 by raising the keyhole member 72 out of the slot 90 on the ventilator surface 86 and then removing the bottom rim 66 from underneath the retaining rim 85 and the second end portion 40 of the central inhalation conduit 30 from the elastomeric ring 80 (FIG. 3). If not bonded together, the respective pressure monitoring tube 76 and patient breathing circuit 26 are manually pulled out of press-fit relationship with their respective ports.

In use, once the adapter 20 is securely mounted to the ventilator 22, it provides a conduit for breathable gas to flow from the ventilator 22 to the patient breathing circuit 26, as shown at arrows 35,37 in FIG. 3. During the inhalation phase, breathable gas from the ventilator outlet 82 enters the adapter 20 at the second end portion 40 of the central inhalation conduit 30. From the inhalation conduit 30 the breathable gas is delivered to the central inhalation conduit 42 of the patient breathing circuit 26 and ultimately to the patient's airway. Referring briefly to FIG. 5, as breathable gas is traveling to the patient, aerosolized medicine from the nebulizer 24 is entrained into the gas flow from the nebulizer conduit 44. Such early introduction of aerosolized medicine into the flow of breathable gas provides better deposition of the aerosolized medicine during the inhalation phase. With the delivery device positioned proximate to the ventilator (i.e. at the distal end of the inspiratory circuit relative to the patient) the bias flow charges the inspiratory circuit during the exhalation phase such that the volume of the inspiratory circuit is used as an aerosol reservoir prior to the delivery to the patient. This advantageously maximizes the aerosolized medicine available to the patient.

Referring back to FIG. 3, once the inhalation phase is complete and the breathable gas is delivered to the patient, the patient exhales and breathed gas is delivered back through the surrounding exhalation conduit 32 of the patient breathing circuit 26. Breathed gas from the surrounding exhalation conduit 32 enters the depending discharge conduit 54, as shown by arrows 37. Close proximity of the exhalation conduit 32 to the inhalation conduit 30 (coaxial in the described embodiment) advantageously facilitates heat transfer from the exhaled gas to warm the inhaled gas/medicine prior to delivery to the patient.

As shown in FIG. 3, the selectively actuated valve 58, depicted in a closed position, comprises a diaphragm 98 which is actuated by a solenoid-powered finger 100. During the inhalation phase, the solenoid 102 is actuated and the finger 100 compresses the diaphragm 98 against the valve seat 104 of base 56 to form an airtight seal and prevent breathed gas from escaping the adapter 20. During the exhalation phase, the solenoid 102 is de-energized and causes the finger 100 to move downward, away from the diaphragm 98, which allows breathed gas to flow between the diaphragm 98 and the valve seat 104 of the base 56. FIG. 5 shows the valve 58 in open position to accommodate breathed gas flow during the exhalation phase. Breathed gas flows from the exhalation conduit 32, to the depending discharge conduit 54, and is exhausted out the discharge conduit 54 to atmosphere, as shown at arrow 106. It should be recognized that breathed gas might also be exhausted to a receptacle or other destination source for breathed gas on a ventilator.

It will thus be seen that the adapter 20 efficiently interconnects a patient's breathing circuit to a ventilator. In the embodiment illustrated the adapter efficiently interconnects the patient breathing circuit, a pressure monitor, a source of aerosolized medicine and the ventilator. The adapter 20 couples the source of aerosolized medicine proximate to the ventilator, and thus distal from the patient with respect to the breathing circuit. In this manner, as described above, improved deposition of aerosolized medicine during the inhalation phase results. During the exhalation phase, the delivery device provides a small bias flow rate while the aerosol delivery device continuously atomizes medicine at a fixed rate. With the delivery device placed proximate to the ventilator, the bias flow charges the inspiratory circuit with aerosol during the expiratory phase, thus maximizing the aerosolized medicine available to the patient during the inspiratory phase.

While this invention is susceptible to embodiments in many different forms, the drawings and the specification describe in detail a preferred embodiment of the invention. They are not intended to limit the broad aspects of the invention to the embodiment illustrated.

I claim:

1. An adapter for removably coupling a patient breathing circuit to a ventilator, said adapter comprising:
   an inhalation conduit having a first end for coupling said adapter to the ventilator and a second end for coupling said adapter to the patient breathing circuit;
   an exhalation conduit having a first end for coupling said adapter to the patient breathing circuit and a discharge conduit, said discharge conduit transversely oriented to said inhalation conduit;
   an exhaust port communicating with said discharge conduit for releasing breathed gas from same;
   a valve selectively opening and closing said discharge conduit to release gas from same; and
   a base comprising means for releasably coupling said adapter to the ventilator.

2. The adapter of claim 1, further comprising:
   a pressure port for coupling a pressure monitor tube to said adapter.

3. The adapter of claim 1, wherein said valve is electromechanically actuated.

4. The adapter of claim 1, wherein said valve comprises a diaphragm which selectively forms a seal with a valve seat on said base.

5. The adapter of claim 1, wherein said valve is solenoid powered.

6. The adapter of claim 1, further comprising:
a medicine delivery conduit communicating with said inhalation conduit intermediate its first and second ends, said medicine delivery conduit for receiving medicine and providing same to said inhalation conduit.

7. The adapter of claim 6, wherein said medicine delivery conduit is adapted to support a medicine delivery device in a vertical orientation.

8. The adapter of claim 7, wherein said medicine delivery device is a nebulizer.

9. The adapter of claim 1, wherein said inhalation conduit and said exhalation conduit are coaxial.

10. An adapter for removably coupling a patient breathing circuit to a ventilator, said adapter comprising:
an inhalation conduit having a first end for coupling said adapter to the ventilator and a second end for coupling said adapter to the patient breathing circuit;
an exhalation conduit having a first end for coupling said adapter to the patient breathing circuit and a discharge conduit, said discharge conduit transversely oriented to said inhalation conduit;
a valve selectively opening and closing said discharge conduit to release breathed gas from same;
an exhaust port through which breathed gas from said discharge conduit is released; and
a base for coupling said adapter to said ventilator, said base comprising a lip and a keyhole, wherein said lip is received by a ledge on the ventilator and said keyhole is received by a slot in the ventilator, and wherein upon insertion of said keyhole into said slot, a spring-biased bar in the ventilator is cammed open and subsequently biased closed through said keyhole to removably couple said adapter to the ventilator.

11. The adapter of claim 10, wherein said valve comprises a diaphragm which selectively forms a seal with a valve seat on said base.

12. The adapter of claim 11, wherein said valve is solenoid powered.

13. The adapter of claim 10, further comprising:
a pressure port for coupling a pressure monitor tube to said adapter.

14. The adapter of claim 10, further comprising:
a medicine delivery conduit communicating with said inhalation conduit intermediate its first and second ends, said medicine delivery conduit for receiving medicine and providing same to said inhalation conduit.

15. An adapter for removably coupling a patient breathing circuit to a ventilator, said adapter comprising:
an inhalation conduit having a first end for coupling said adapter to the ventilator and a second end for coupling said adapter to the patient breathing circuit;
an exhalation conduit having a first end for coupling said adapter to the patient breathing circuit and a discharge conduit, said discharge conduit transversely oriented to said inhalation conduit;
a pressure port for coupling a pressure monitor tube to said adapter;
a valve selectively opening and closing said discharge conduit to release breathed gas from same;
an exhaust port through which breathed gas from said discharge conduit is released; and
a base comprising means for releasably coupling said adapter to the ventilator.

16. The adapter of claim 15, wherein said valve comprises a diaphragm which selectively forms a seal with a valve seat on said base.

17. An adapter for removably coupling a patient breathing circuit to a ventilator, said adapter comprising:
an inhalation conduit having a first end for coupling said adapter to the ventilator and a second end for coupling said adapter to the patient breathing circuit;
an exhalation conduit having a first end for coupling said adapter to the patient breathing circuit and a discharge conduit, said discharge conduit transversely oriented to said inhalation conduit, wherein said inhalation and exhalation conduits are coaxial;
a medicine delivery conduit communicating with said inhalation conduit intermediate its first and second ends, said medicine delivery conduit for receiving medicine and providing same to said inhalation conduit;
a pressure port for removably coupling a pressure monitor tube to said adapter;
a electro-mechanically actuated valve selectively opening and closing said discharge conduit to release breathed gas from same;
an exhaust port through which breathed gas from said discharge is released; and
a base for coupling said adapter to said ventilator, said base comprising a lip and a keyhole, wherein said lip is received by a ledge on the ventilator and said keyhole is received by a slot in the ventilator and wherein upon insertion of said keyhole into said slot, a spring-biased bar in the ventilator is cammed open and subsequently biased close through said keyhole to removably couple said adapter to the ventilator.

* * * * *